United States Patent [19]

Foote

[11] Patent Number: 5,661,028

[45] Date of Patent: Aug. 26, 1997

[54] LARGE SCALE DNA MICROSEQUENCING DEVICE

[75] Inventor: Robert S. Foote, Oak Ridge, Tenn.

[73] Assignee: Lockheed Martin Energy Systems, Inc., Oak Ridge, Tenn.

[21] Appl. No.: 536,010

[22] Filed: Sep. 29, 1995

[51] Int. Cl.[6] .......................... C12M 1/00; C12N 15/00; B60R 9/00; C07H 21/04
[52] U.S. Cl. .................. 435/287.2; 435/6; 435/91.1; 536/24.3; 935/78; 935/85; 204/450; 204/456; 216/39; 423/324
[58] Field of Search ................ 435/6, 91.1, 270, 435/183, 287.2, 287.9, 288.2, 288.4, 288.7; 536/23.1, 24.3, 24.33, 25.3; 935/77, 78, 85; 204/456, 450; 422/101, 149, 50, 68.1; 423/324; 216/2, 39, 56, 89

[56] References Cited

U.S. PATENT DOCUMENTS

| | | | |
|---|---|---|---|
| 4,908,112 | 3/1990 | Pace | 204/299 R |
| 5,073,239 | 12/1991 | Hjerten | 204/180.1 |
| 5,092,973 | 3/1992 | Zare et al. | 204/182.1 |
| 5,110,431 | 5/1992 | Moring | 204/180.1 |
| 5,141,621 | 8/1992 | Zare et al. | 204/299 |
| 5,279,721 | 1/1994 | Schmid | 204/182.8 |
| 5,288,468 | 2/1994 | Church et al. | 422/116 |
| 5,302,509 | 4/1994 | Cheeseman | 435/6 |

FOREIGN PATENT DOCUMENTS

| | | |
|---|---|---|
| 0 356 160 | 2/1990 | European Pat. Off. |
| 2 191 110 | 9/1987 | United Kingdom. |
| 92/07678 | 3/1993 | WIPO. |
| 9200587 | 5/1993 | WIPO. |
| 93/00697 | 10/1993 | WIPO. |

OTHER PUBLICATIONS

*Micromachining a Miniaturized Capillary electrophoresis- -Based chemical Analysis System on a Chip* (Science Reports ● vol. 261 ● 13 Aug. 1993; pp. 895–897).

*Primary Examiner*—Bradley L. Sisson
*Attorney, Agent, or Firm*—Shelley L. Stafford

[57] ABSTRACT

A microminiature sequencing apparatus and method provide means for simultaneously obtaining sequences of plural polynucleotide strands. The apparatus comprises a microchip into which plural channels have been etched using standard lithographic procedures and chemical wet etching. The channels include a reaction well and a separating section. Enclosing the channels is accomplished by bonding a transparent cover plate over the apparatus. A first oligonucleotide strand is chemically affixed to the apparatus through an alkyl chain. Subsequent nucleotides are selected by complementary base pair bonding. A target nucleotide strand is used to produce a family of labelled sequencing strands in each channel which are separated in the separating section. During or following separation the sequences are determined using appropriate detection means.

25 Claims, 5 Drawing Sheets

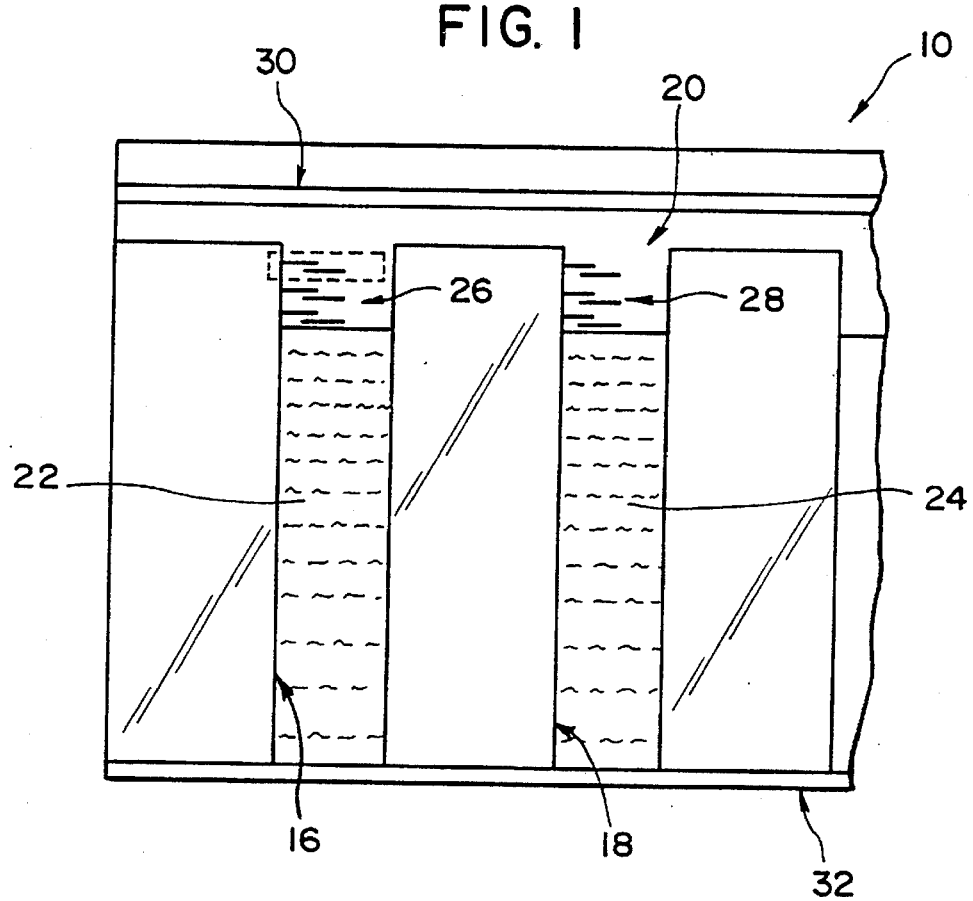
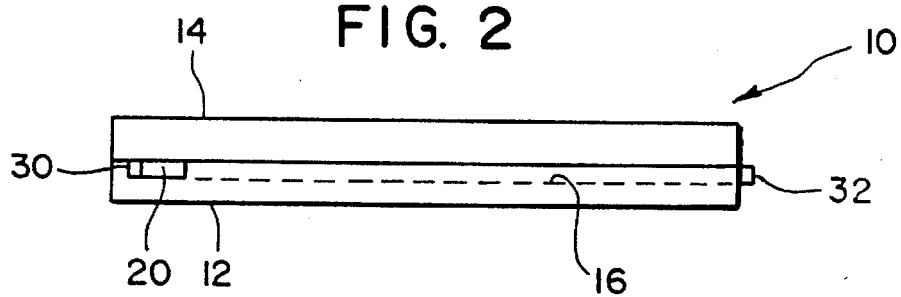
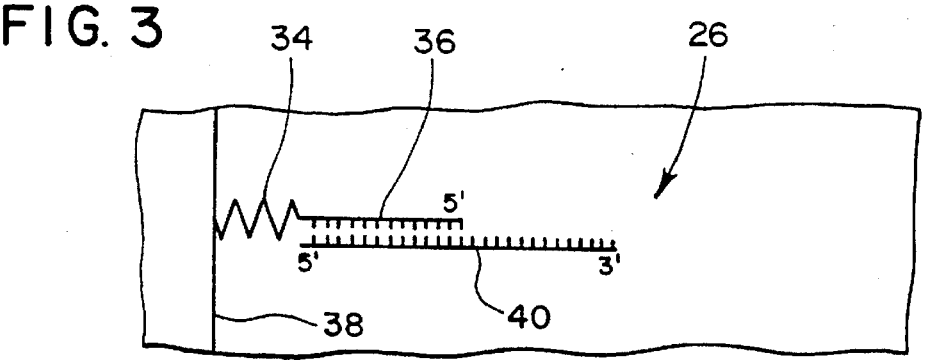

etc.

LARGE SCALE DNA MICROSEQUENCING DEVICE

This invention was made with Government support under contract DE-AC05-84OR21400 awarded by the U.S. Department of Energy to Lockheed Martin Energy Systems, Inc. and the Government has certain rights in this invention.

FIELD OF THE INVENTION

The present invention relates generally to sequencing polynucleotides and more specifically to the simultaneous parallel sequence determination of the sequences of a large plurality of polynucleotides. Arrays of oligonucleotide probes are covalently bonded to multiple parallel lanes etched into a glass microchip device. Hybridization, synthesis and subsequent electrophoresis all occur within the one device to determine the large plurality of sequences.

Each array comprises multiple copies of a species of oligonucleotide primers. The primers act similar to an oligonucleotide probe, used in Southern or Northern blotting, to select the target polynucleotide for sequencing and the same oligonucleotide species strand also serves as a primer for the synthesis of a nucleotide strand. Each newly synthesized strand is complementary to the target polynucleotide by hydrogen bonding between opposite strand basepairs. Any template based sequencing reaction can be used, including Maxam-Gilbert or Sanger reactions.

BACKGROUND OF THE INVENTION

Since the cracking of the genetic code in the middle of the twentieth century, determining the base sequences of DNA and RNA has been a tool for elucidating the primary structure of peptides and proteins. Sequence information is also useful for determining gross polynucleotide structure and control of gene expression. The base sequences of non-coding polynucleotide regions are also useful for studying mutation events, phylogenetic linkages, polynucleotide structural characteristics, cell cycle control, cancer and transcription and translation mechanisms.

Two sequencing methods are commonly used: the Maxam-Gilbert, or chemical degradation method, and the Sanger, or dideoxy terminator or enzymatic method. Either method delivers a family of DNA strands. Each strand species is incrementally longer by one base than the next smaller species. By tagging the strands to indicate which nucleotide is additional to the next smaller strand species, the sequence of bases of the polynucleotide can be determined. Gel electrophoresis is commonly used to resolve the different lengths for analysis and determination of sequence.

During the sequencing reaction each polynucleotide strand can be tagged by labelling the primers, by labelling the terminal base itself, or by labelling a plurality of one base incorporated into each strand.

Two common labelling methods are the use of radioisotopes and fluorescent tags. Using a different fluorescent tag for each terminal base allows sequencing analysis to be accomplished in a single electrophoresis lane. Other methods require multiple parallel lanes for sequencing one polynucleotide fragment.

For example, the original Sanger method required four (4) parallel reaction vessels. Each vessel was identical except for the terminating dideoxy base included in the reaction mixture. Thus when products from the four vessels were electrophoresed in four parallel lanes, each lane revealed only the DNA strands terminating in the respective dideoxy base. By comparing the four lanes containing a DNA ladder of lengths of DNA differing by only one base and knowing the terminating base of each lane, the sequence could be determined.

Another method being developed uses non-radioactive isotopic labels and mass spectrometry to determine the polynucleotide sequence.

At present the most automated systems use either Sanger or Maxam-Gilbert sequencing chemistry, and tag the resultant DNA species with fluorescent probes. On line detection is accomplished as each band is electrophoresed past a detection window. Commercial embodiments of this technology, however, are limited to thirty-six or fewer simultaneous sequence determinations per electrophoresis plate.

An automated electrophoresis apparatus is described in U.S. Pat. No. 5,279,721 to Schmid. Molecules are electrophoretically separated, based on molecular weight, by a horizontal electric field. An impermeable sheet is then removed allowing a vertical electrical field to effect transfer of the separated substances to a blot membrane.

While automating some aspects of electrophoresis and electroblotting, the apparatus described in U.S. Pat. No. 5,279,721 does not sequence a polynucleotide or provide means for the required multiple serial reactions. Rather, it addresses Southern blotting procedures wherein specific nucleotide sequences are detected by complementary binding with a probe nucleotide strand.

Another method, described in U.S. Pat. No. 5,302,509 to Cheeseman, uses a solid support to anchor a DNA template to the apparatus and determines each complementary base species as it is added during the synthesis process. This method does not describe gel electrophoresis for separation.

Solid phase supports are also described in WO 93/20232. Here two or more regions of target DNA could be sequenced by annealing them to opposite selective sequencing primers. A modified Sanger reaction followed. In a preferred embodiment formamide was used to chemically melt the DNA from the Dynabead supports before electrophoresis into the separating gel. This method lends itself to PCR amplification of very small quantities of DNA prior to the sequencing reactions.

These and other sequencing schemes are advancing due to the impetus of the human genome project. The goal of the genome project, to sequence the entire human genome (and selected genes of other species) has been likened to the 1960's era space program to put a man on the moon by the end of the decade. Many researchers are therefore proposing methods to rapidly and inexpensively sequence massive lengths of genetic materials. Reducing the costs and errors inherent in human manipulations is a common thread of these proposals.

SUMMARY OF THE INVENTION

The present invention provides a novel microchip based apparatus and method for sequencing massively multiple polynucleotide strands with a minimal requirement for human intervention. Techniques borrowed from the microelectronics industry are particularly suitable to these ends.

Micromachining and photolithographic procedures are capable of producing multiple parallel microscopic scale components on a single chip substrate. Materials can be mass produced and reproducibility is exceptional. The microscopic sizes minimize material requirements.

Human manipulations can be minimized by designing and building a dedicated apparatus capable of performing a series of functions. For example, DNA sequencing requires: 1) selection and purification of the target DNA strand, 2) labeling the strand in a manner to permit sequencing, 3) producing a family of strands beginning with a specified base from the target DNA strand and terminating at every incremental base along the sequencing region of the strand to be sequenced, 4) separating a mixture of strands differing in length by one base, and 5) identifying the last incremental base.

The present invention proposes a novel microchip based apparatus and method for accomplishing these procedures on the single microchip. Sequencing massively multiple polynucleotide strands economically and with a minimal requirement for human intervention is thus feasible.

An object of the present invention is to provide a massively parallel automated DNA sequencing method and apparatus in which multiple serial reactions are automatically performed individually within one reaction well for each of the plural polynucleotide strands to be sequenced in the plural parallel sample wells. These serial reactions are performed in a simultaneous run within each of the multiple parallel lanes of the device. "Parallel" as used herein means wells identical in function. "Simultaneous" means within one preprogrammed run. The multiple reactions automatically performed within the same apparatus minimize sample manipulation and labor.

A further object of this invention is to provide an apparatus and method wherein a plurality of samples can be simultaneously processed to determine a polynucleotide sequence for each sample.

Another object of the invention is to provide selection means within each well to uniquely select the target polynucleotide to be sequenced.

Yet another object of the present invention is to provide a means for segregating sequencing reactions in a small undivided volume, thereby conserving reagents and enzymes.

Another object of the present invention is to provide a miniaturized electrophoresis system for separation of nucleotides or other molecules based on their electrophoretic mobilities. The miniaturization allows sequence determination to be accomplished using very small amounts of sample.

Still another object of the invention is to provide multiple reaction wells, the reaction wells being reaction chambers, on a microchip, each reaction well containing an individualized array to be used for determining the nucleotide sequence uniquely specified by the substrates provided, the reaction conditions and the sequence of reactions in that well.

Some objects of Applicant's invention are met by an apparatus for performing DNA sequencing comprising a body, a channel pattern formed within the body and including at least one gel channel. The gel channel has first and second longitudinal ends and are at least partially filled with gel. The apparatus further comprises a reaction chamber in communication with the gel and having a surface for attachment of DNA synthesis primers. The apparatus further comprises means for communicating a solution containing at least one target DNA to the reaction chamber for hybridization with the DNA synthesis primers, and means for establishing an electric field between the first and second longitudinal ends of the at least one gel channel, of sufficient strength to impart electrophoretic separation of chain-terminated strands of DNA through the gel.

Other objects of Applicant's invention are met by a method of making a microchip used in making a DNA sequencing analysis comprising the steps of a) forming a channel pattern in a planar surface of a substrate wherein the channel pattern includes at least one gel channel; b) fixedly attaching a planar surface of a cover plate on the planar surface of the substrate; c) partially filling the at least one gel channel with a gel and thereby forming a reaction chamber in the unfilled portion; and d) placing first and second electrodes respectively at opposite ends of the at least one gel channel.

Still, other objects are met by an apparatus for simultaneously sequencing a plurality of polynucleic acids comprising a solid support substrate, a plurality of sequencing channels wherein each channel has a reaction well and a separating zone. The apparatus further comprises means for delivering and flushing substances to each reaction well; means for specifically selecting and binding a predetermined target sequence within the reaction well of each channel; means for individually controlling sequencing reactions in each reaction well; means for detaching polynucleotide strands from the solid support substrate; means for applying an electrophoretic voltage across the separating zone; and means for monitoring the electrophoretic separation to determine a sequence of a polynucleic acid from the target sequence in each reaction well.

In accordance with yet other objects of Applicant's invention, a method for sequencing polynucleic acids comprises the steps of a) placing a DNA probe capable of acting as a DNA synthesis primer in a reaction chamber juxtaposed at least one gel electrophoresis lane; b) introducing into the reaction chamber a target DNA containing a sequence complementary to the DNA probe, and thereby allowing the DNA probe and the target DNA to hybridize; c) introducing into the reaction chamber reagents, labeling means and enzymes for dideoxy sequencing, and allowing sequencing reactions to form labelled terminated chains; d) separating the labelled terminated chains from the target DNA; and e) applying a voltage across at least one gel electrophoresis lane to electrophoretically separate the labelled terminated chains.

Other objects are met by a method for sequencing polynucleic acids comprising the steps of a) placing a DNA probe capable of selecting a target DNA sequence in a reaction chamber juxtaposed at least one gel electrophoresis lane; b) introducing into the reaction chamber a target DNA containing a sequence complementary to the DNA probe, and thereby allowing the DNA probe and the target DNA to hybridize; c) introducing into the reaction chamber reagents, and labeling means for chemical degradation sequencing, and allowing sequencing reactions to form shortened sequencing chains; d) separating the shortened sequencing chains from the probe DNA; and e) applying a voltage across the at least one gel electrophoresis lane to electrophoretically separate the shortened sequencing chains.

In accordance with still yet other objects of Applicant's invention, a method of sequencing a target DNA sequence comprises the steps of a) placing a plurality of probe/primers respectively in corresponding reaction chambers, each probe/primer having a unique and defined sequence which allows the probe/primer to hybridize to a specific sequence, at different locations, in the target DNA and to act as a primer for DNA sequencing reactions; b) forming a gel channel respectively in communication with corresponding ones of the reaction chambers; c) adding a solution containing the target DNA sequence to the reaction chambers; d) adding reagents and labeled enzymes to permit dideoxy reactions which form chain terminated labeled strands initiated at different locations of the target DNA; e) separating labeled strands; and f) analyzing the separated strands for DNA sequence.

The invention accomplishes the aforementioned operations on a single device with a minimum of human intervention and handling. The microchip is preferably transparent, thereby allowing photochemical reactions to be controlled individually within each of the large plurality of lanes using automated equipment and a preprogrammed protocol and also allowing detection of fluorescently labelled strands.

Other objects, advantages and salient features of the invention will become apparent from the following detailed description, which taken in conjunction with the annexed drawings, discloses preferred embodiments of the invention.

BRIEF DESCRIPTION OF THE DRAWINGS

FIG. 1 is a top schematic view of a microchip according to a preferred embodiment of the present invention;

FIG. 2 is an end view of the microchip of FIG. 1;

FIG. 3 is an enlarged view of the area delineated by the broken line rectangle of FIG. 1;

DETAILED DESCRIPTION OF THE INVENTION

Figure 4A:
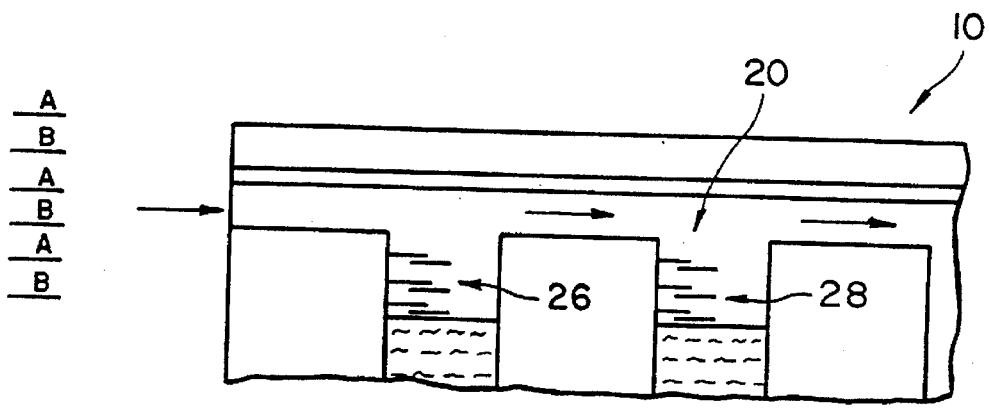
FIGS. 4(a)-(d) sequentially illustrate the sequencing methodology of the present invention.

Referring to FIGS. 1 and 2, a microchip 10 for performing large-scale microsequencing of DNA includes a substrate 12 and a cover plate 14 bonded thereto. A channel pattern, etched into an upper surface of the substrate, includes a plurality of parallel channels 16 and 18 interconnected for fluid communication at a common end through at least one manifold connecting channel 20. The number of parallel channels can range from one to 1,000 or more.

The substrate 12 is preferably made of biocompatible material that is transparent to light, including glass and quartz. Silicon, plastics and ceramics may also be used. In one particular embodiment, the substrate 12 is a 3 cm long by 1 cm wide by 0.25 cm thick microscope slide. The cover plate 14 is also preferably transparent and may, for example, be a microscope slide or cover slip of similar dimensions to the substrate 12.

The channel pattern is formed in the glass substrate 12 using standard photolithographic procedures followed by chemical wet etching. Standard photolithographic procedures include transferring the pattern to the substrate using a positive photoresist (Shipley 1811) and an e-beam written chrome mask (Institute of Advanced Manufacturing Sciences, Inc.). Wet etching includes using a $HF/NH_4F$ solution. A similar channel forming technique can be found in a patent application by Ramsey to a microminiature capillary zone electrophoresis apparatus, Ser. No. 08/283,769, incorporated herein by reference. Micromachining techniques may alternatively be employed to form the channel pattern.

The parallel channels 16 and 18 are approximately 50 μm in width and approximately 10 to 20 μm in depth. The length can be longer than the glass substrate and up to a few cm by forming the channels in a serpentine shape. A thousand or more parallel channels can be formed on the microchip as described herein. The manifold connecting channel 20 is perpendicular to the parallel channels and is 50 to 100 μm wide and approximately 10 to 20 μm in depth.

After forming the channel pattern on the substrate 12, the cover plate 14 is bonded to the top surface of the substrate 12 using a direct bonding technique whereby the cover plate 14 and the substrate 10 are first hydrolyzed in dilute $NH_4OH/H_2O_2$ solution and then joined. The assembly is then annealed at about 500° C. in order to insure proper adhesion of the cover plate 14 to the substrate 12. The cover plate 14 thus encloses the channels etched (machined, or otherwise formed) in the upper surface of the substrate 12.

In the preferred embodiment, an acrylamide buffer solution is electro-osmotically pumped through the manifold connecting channel 20 into the parallel channels 16 and 18. A volume of separating gel 22 and 24 is formed within each parallel channel 16 and 18, respectively, by photopolymerizing the acrylamide solution within the parallel channels.

Acrylamide in the manifold connecting channel 20 and an approximately 50 μm length of each parallel channel at the intersection with the manifold connecting channel 20 is not photo-irradiated so that the acrylamide contained therein is not polymerized. The non-polymerized acrylamide can be flushed from the system with an appropriate wash buffer. Flushing can be accomplished by electro-osmotic pumping, by electrophoretic pumping or by a pressure gradient. Typical electric field strengths range from 200 to 700 V/cm but may range from 50 to 1500 v/cm.

Approximately 50 μm wide by 50 μm long by 20 μm deep reaction wells 26 and 28 are thus formed at one end portion of each parallel channel 16 and 18, respectively. Most of the remaining length of each parallel channel 16 and 18 provides a separating zone which is used for electrophoretic separation of the products formed in the reaction wells, reaction chambers, 26 and 28.

First and second electrodes 30 and 32 are disposed, respectively, in the manifold connecting channel and at opposite ends of the parallel channels 16 and 18. The second electrode 32 is shown in direct contact with the gel 22 and 24 but may be separated from it by an electrically conducting solution. An electric potential established at the two electrodes, and the electric field established therebetween, provides the motive force for electrophoretic manipulations, to be described more fully below.

The manifold connecting channel 20 is used for delivering polynucleotides, reagents, wash solutions, buffers and the like to the reaction wells 26 and 28. Additional manifold connecting channels can be used also for delivering additional reagents, wash solutions, buffers and the like to the reaction wells. In the preferred embodiment, the ends of the manifold connecting channel are connected to fluid reservoirs and the various solutions, reagents and the like are electro-osmotically or electrophoretically transported through the channel to the reaction wells by applying electric potentials to reservoirs at opposite ends of the channel. Alternatively, a pressure gradient may be used to transport solutions through the channel. Reagents, etc. are added at one end of the channel and wastes are collected at the other end. In an alternative embodiment, a second manifold connecting channel, parallel to the first manifold connecting channel 20 from FIGS. 1 and 2 may be disposed between the reaction wells and the separating zones of each of the sequencing channels. Reagents, wash solutions, etc. may then be transported from one of the manifold channels to the other manifold channel through the reaction wells by applying an electric potential difference or a pressure gradient between the two channels. In a further alternative embodiment, the cover plate 14 may be provided with access ports allowing the use of micropipetting procedures, preferably robotic, to introduce substances into the reaction wells. Each reaction well 26 and 28 acts as a hybridization/synthesis chamber, a reaction chamber and contains probe/primer oligonucleotides of defined sequence, and immobilized as shown in FIG. 3. As seen therein, a linker 34, preferably an alkyl chain 10 to 20 carbons in length, is shown covalently attaching the 3' end of a oligonucleotide strand 36 to a surface 38 of the substrate 12 (or cover plate 14). Surface 38 is a longitudinal sidewall of the parallel channel 16. Several such alkyl linkers 34 are provided in each reaction well, as shown in FIG. 1.

The linker oligonucleotides 36 in each specific reaction well have a unique sequence which allows them to hybridize with the 5' end of a specific probe/primer oligonucleotide 40 via hydrogen-bonding of complementary base pairs according to Watson-Crick base-pair rules. The 3' overhanging end of the probe/primer 40 also has a unique sequence which allows it to hybridize to a specific sequence in the target DNA and to act as a primer for DNA sequencing reactions.

The alkyl linkers may be attached through a Si—C direct bond or through an ester, Si—O—C, linkage Maskos and Southern, *Nucleic Acids Research*, 20: 1679–1684, 1992). The alkyl linker may contain backbone atoms other than carbon to provide additional reaction or cleavage sites. An example using a 2-nitrobenzyl derivative for photocleaving means is described by Pillai in *Organic Photochemistry*, Vol. 9, Albert Padwa, Ed., Marcel Dekker, Inc. pp. 225–323, 1987, incorporated herein by reference.

An alternate method for attaching oligonucleotides to glass is described by Graham et al. See *Biosensors & Electronics*, 7: 487–493, 1992.

As many as $10^6$ linker oligonucleotides per $\|m^2$ may be attached, though steric considerations may warrant a lower density. These oligonucleotides are preferably synthesized in situ by photochemical methods, examples of which are described in *Organic Photochemistry*.

A simple binary method allows multiple simultaneous, spatially localized, parallel syntheses of $2^n$ compounds in n steps is described by Fodor, et al., *Science* 251: 767–773, 1991. For example approximately 65,000 different oligonucleotides, the total number of 8-mers using four nucleotide bases, could be synthesized by these techniques is 32 chemical steps. On a smaller scale the approximately 1000 unique 5-mers could be synthesized in 20 steps.

The photochemistry involves protection of the 5' hydroxyl group of nucleosides or nucleotides with a protecting group to prevent undesirable chemical reactions. The protecting group preferably is a selectively removable chemical compound. Most preferably it is photolabile. The group can be any moiety which undergoes photolysis to regenerate the 5' alcohol. Groups suitable for blocking may be found in: Pillai, Photolytical Deprotection and Activation of Functional Groups, *Organic Photochemistry*, Albert Padwa Ed. Vol. 19 Chapter 3, pp. 225–323, 1987; Pillai, Photoremovable Photoprotecting Groups in Organic Synthesis, *Synthesis*, 1980 p. 1–26; *Organic Synthesis a Practical Approach*, M. J. Gait Ed. IRl Press, Oxford, Washington, D.C., 1984; incorporated herein by reference.

Such a synthesis protocol using nominal 50 µm lanes allows packing approximately 100 lanes each with a different oligonucleotide for each linear cm of glass substrate. A plurality of sequencing channels can number from between 50 and 10,000 and each sequencing channel can range from 10 to 100 µm in width.

As seen in FIG. 3, the probe/primer oligonucleotide 40 is shown attached by its 5' end portion, to the 5' end portion of the linker oligonucleotide 36 by complementary hydrogen bonding. Preferably, the linker oligonucleotide 36 is 10 to 15 nucleotides in length and is complementary to approximately the same number of nucleotides at the 3' terminal portion of the probe/primer oligonucleotide 40.

The 3' end portion of the probe/primer 40 includes a unique sequence of 8 to 20 nucleotides complementary to the 3' terminal portion of the target sequence. The unique sequence of the probe/primer 3' terminal portion uniquely selects the target polynucleotide for processing in each reaction well. An oligonucleotide eight bases in length has ~65,000 different possibilities using one of four possible bases at each position. Similarly, an oligonucleotide fifteen bases in length has over 1 billion different sequences possible.

Sequencing Methodology

FIGS. 4(a)–(d) illustrates sequentially the steps undertaken to effect a DNA sequencing operation. As seen in FIG. 4(a), a solution containing different target DNA sequences "A" and "B" is added to reaction wells 26 and 28 through the manifold connecting channel 20. The direction of flow is indicated by the directional arrows.

Figure 4B:
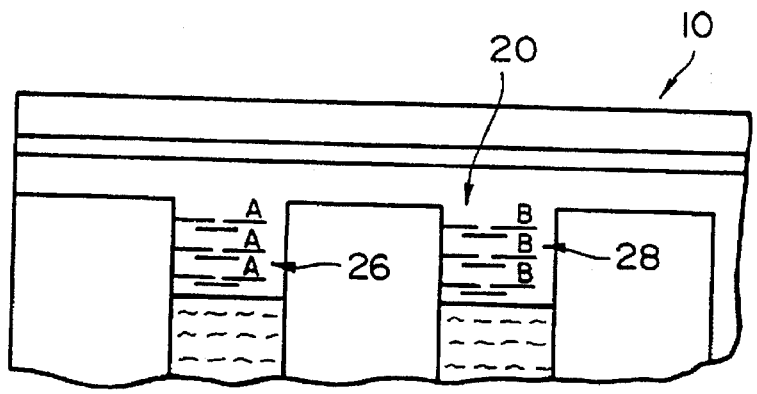

In FIG. 4(b), A and B hybridize to specific probe/primers in reaction wells 26 and 28, respectively. In particular, the target sequence specific to the each of the reaction wells 26 and 28 are selected from a mixture of target sequences by complementary hydrogen bonding of the 3' end portion of the probe/primer 40 to the 3' end portion of the target sequence A or B. The 3' end of the probe/primer serves as a primer site for polynucleotide synthesis using the target sequence as a template.

Once each probe/primer is bound to its specific target sequence, non-hybridized DNA is eluted by flushing the reaction wells. The eluted DNA molecules include extra copies of the target sequence, the target sequences specified by the probe/primers in the other wells, and sequences not targeted.

Figure 4C:
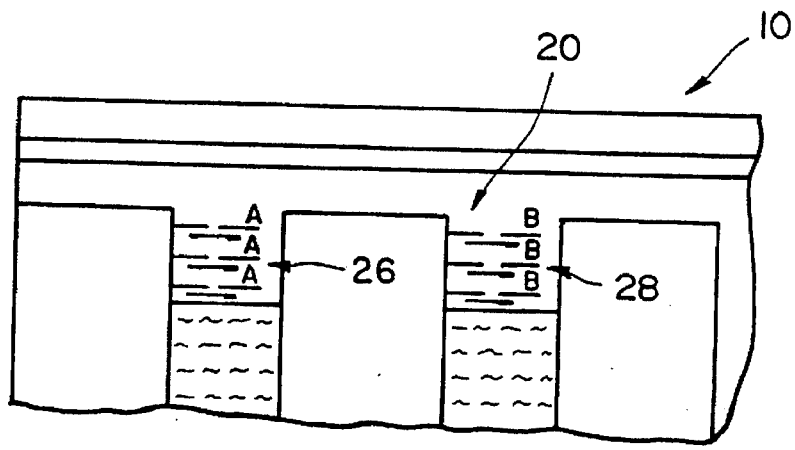

In the next step, FIG. 4(c), reagents and enzyme for dideoxy (Sanger) sequencing are added and sequencing reactions are allowed to occur. The reactions are manifest by elongation (shown as heavy line segments) of the probe/primers 40, which terminate via dideoxy sequencing methods using labeled dNTP's or ddNTP's. Single-lane sequencing of a specific target DNA would require distinguishable ddNTP labels. The deoxy- or dideoxynucleotide triphosphates (dNTP's or ddNTP's) may be labeled with fluorescent groups or other detectable labels or markers.

Either the Maxam-Gilbert sequencing procedure or Sanger dideoxy sequencing methods can be used for polynucleotide sequencing reactions. When using the Maxam Gilbert procedure, either the target sequence itself is degraded, or alternatively, a sequence complementary to the target sequence can be synthesized and then degraded.

Figure 4D:
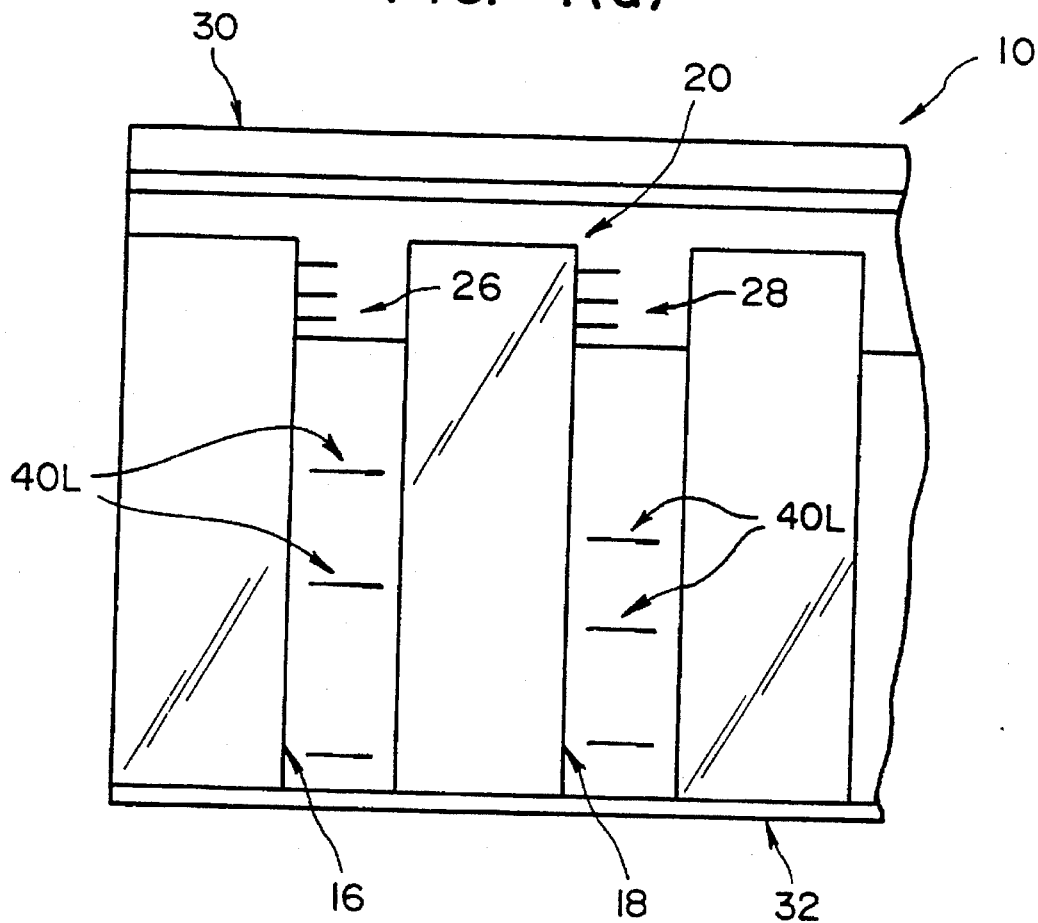

In the next step, illustrated in FIG. 4(d), the DNA is denatured (hydrogen bonds between strands are broken) and the labeled chain-terminated sequencing strands 40L are separated in the gel-containing channels 16 and 18 for detection.

Denaturing can be accomplished using thermal or chemical means to melt the sequencing strand 40L from the linker oligonucleotide and the target DNA. A voltage is then applied across the electrodes 30 and 32 to separate the differently lengthed dideoxy terminated or chemically degraded strands 40L.

Figure 5A:
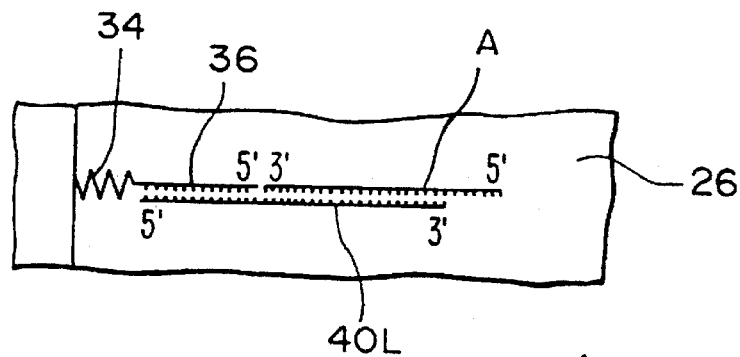
FIGS. 5(a) and 5(b) are enlarged views of a labeled, dideoxy terminated strand 40L before and after denaturing, respectively.
Figure 5B:
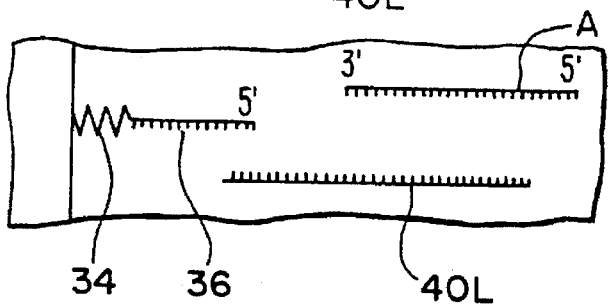

FIGS. 5(a) and 5(b) are enlarged views of a strand 40L. FIG. 5(a) shows all fragments attached, after chain-termination sequencing reactions. Following denaturing, as seen in FIG. 5(b), the target DNA sequence A separates from the labeled, dideoxy terminated strand 40L, which also separates from the linker oligonucleotide 36. Both separated fragments pass by electrophoresis into the gel channel, but only the labeled fragment is detectable (because of the label or marker).

Figure 6A:
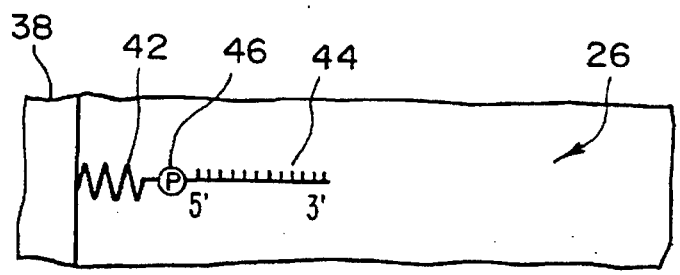
FIGS. 6(a)-(f) sequentially illustrate a sequencing method of an alternative embodiment of the present invention, using photocleaving.

An alternative embodiment is shown in FIGS. 6(a)–(f). In FIG. 6(a), a photocleavable linker 42 is shown attaching a probe/primer oligonucleotide 44 to the surface 38 of the glass substrate through a photocleavable group ("P") 46. Other suitable cleavable linker groups are those cleaved by mild chemical treatment. A restriction site built into the probe/primer oligonucleotide 44 could serve the same function as the photocleavable group 46.

Figure 6B:
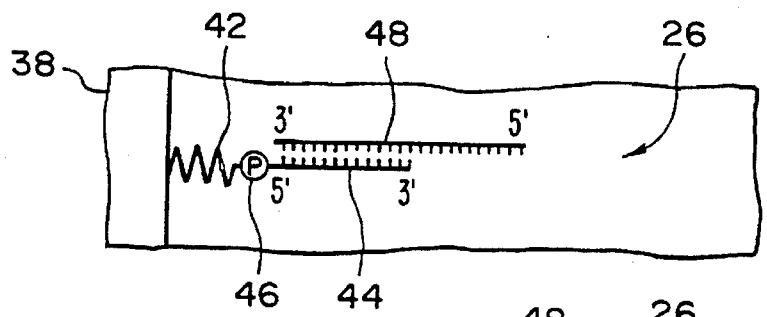
Figure 6C:
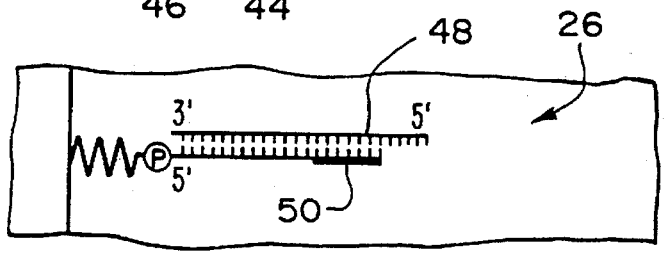

In the next step, illustrated in FIG. 6(b), target polynucleotide 48 is pumped through the manifold connecting channel 20 (FIG. 1) and complementarily binds to the specific probe/primer 44 within the reaction chamber 26. Next, as shown in FIG. 6(c), introduction of reagents and enzymes through manifold connecting channel 20 (after flushing out excess target nucleotide) produces a dideoxy sequencing reaction, which in turn produces a terminated chain 50.

Figure 6D:
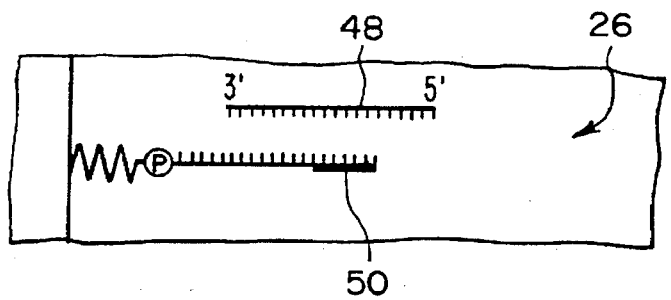
Figure 6E:
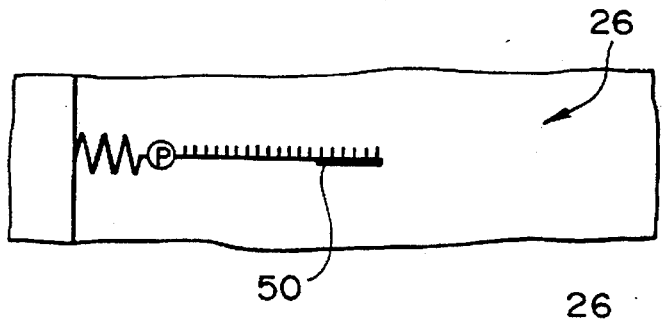
Figure 6F:
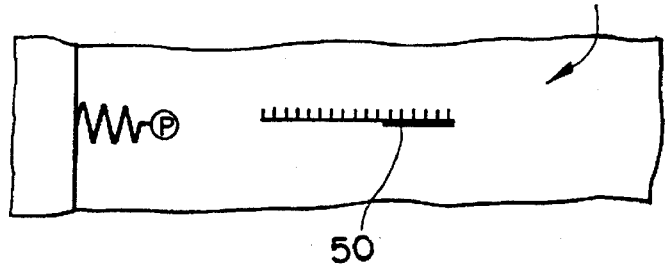

As seen in FIGS. 6(d) and (e), the target DNA sequence is thermally or chemically melted away from the terminated chain 50 and flushed from the reaction well. The elongated probe/primer which is now the terminated strand 50 is detached from the surface 38 by photolysis or a restriction enzyme, as seen in FIG. 6(f). The family of terminated strands 50 are then separated by electrophoresis.

For the embodiment of FIGS. 6(a)–(f), the photocleavable linker 42 can be —(CH$_2$)$_n$—, —(CH$_2$CH$_2$O)$_n$—, etc. and the photocleavable group 46 can be 2-nitrobenzyl or 2-nitrobenzyloxycarbonyl, for example.

For Maxam-Gilbert sequencing, the target strand is selected by the complementary probe oligonucleotide and degraded.

For Sanger sequencing, the captured target sequence serves as a template for a polymerization reaction primed by the primer portion of the capturing strand.

Enzymes and reagents are transferred by electrical or mechanical means to the reaction wells. In the preferred embodiment Sanger sequencing uses fluorescently labeled chain terminators. The fluorescent labels have sufficiently different spectral characteristics such that the terminal base can be identified by these spectral characteristics alone when all four terminators are run in a single lane.

The preferred labelling method is a method using a family of fluorescent terminator compounds of similar electromobility such that the terminator does not interfere with separation and that each base has a unique fluorescent signature either using a single excitation wavelength or plural excitation bands.

Figure 7:
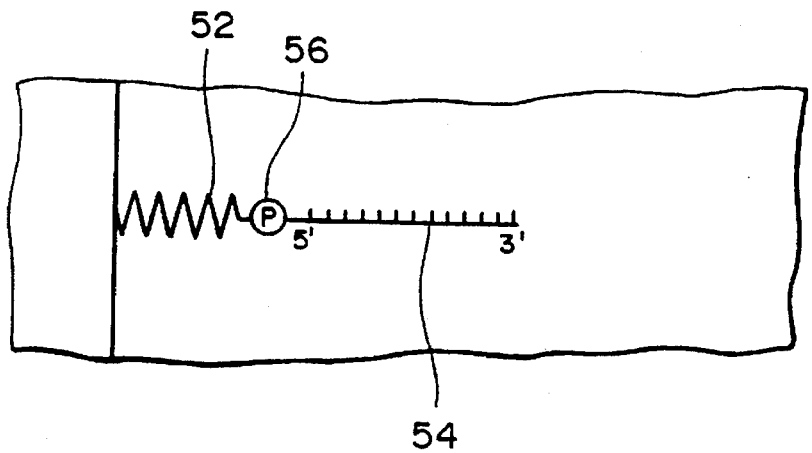
FIG. 7 is a view similar to FIG. 3, showing an alternative embodiment, where a single oligonucleotide sequence acts as a linker/probe/primer and has a photocleavable linker group.

FIG. 7 illustrates another embodiment, in which the functions of the linker oligonucleotide are combined with the functions of the probe/primer oligonucleotide. Here, the attachment polarity of the oligonucleotide is reversed. The probe/primer 54 is attached by its 5' end to the linker 52, thus leaving the 3' end free to complementarily react with a target polynucleotide. The target polynucleotide is thus bound by its 3' portion and the synthesis reactions can use the 3' end of the probe/primer 54 to prime the sequencing synthesis reaction.

An additional requirement of this alternative embodiment is a means to free the elongated probe/primer from the glass substrate. The target strand is removed by melting the polynucleotide strands apart, then flushing the reaction wells to leave only the single strand polynucleotide covalently attached to the microchip surface. A cleavable site 56 can either be built into the linker attaching the probe/primer to the glass substrate or a site cleavable by a restriction enzyme can be included in the probe/primer.

Figure 8:
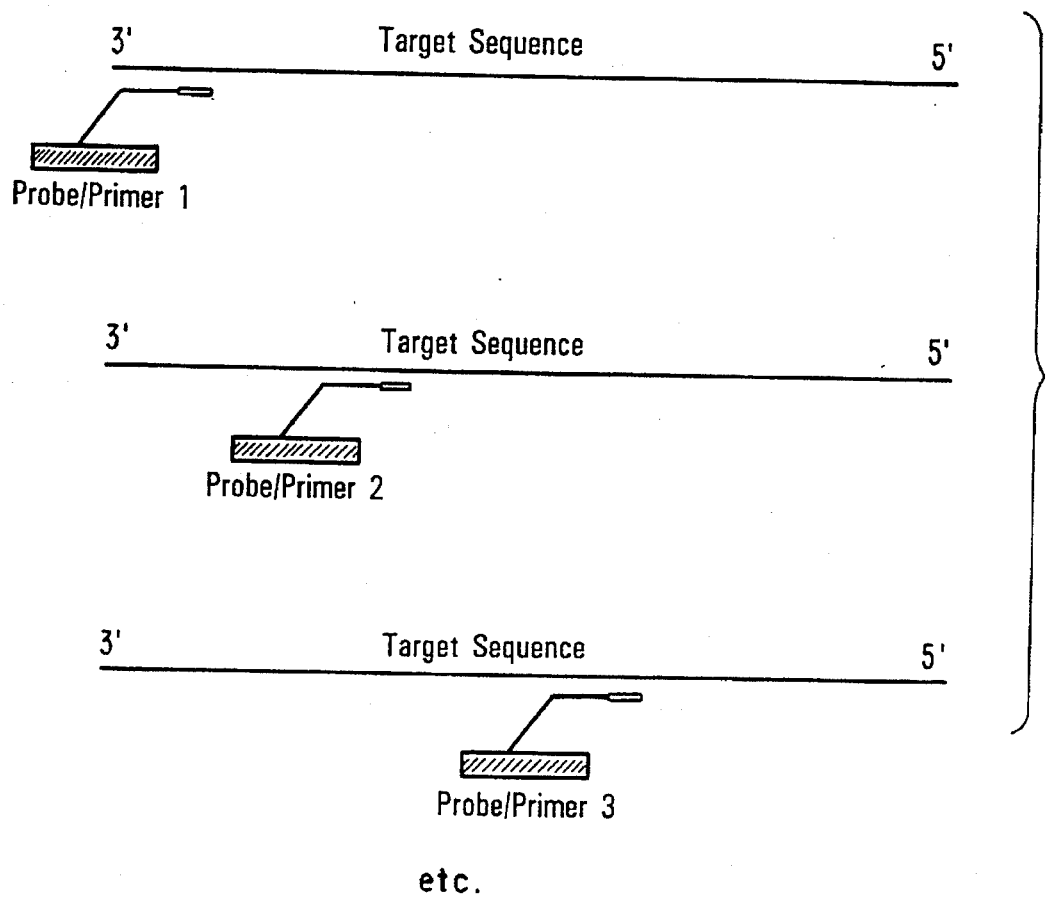
FIG. 8 is a schematic view showing sequencing of a single target DNA strand at different locations using different probe/primers.

In still another embodiment, as shown in FIG. 8, the probe/primer need not bind the 3' end portion of the target polynucleotide, rather the probe/primer may be synthesized to be a sequence complementary to an internal portion of the target polynucleotide sequence. The 3' portion of the target polynucleotide will remain single stranded and unbound to the primer oligonucleotide portion. The 3' terminus of the primer can still use the remaining 5' terminal portion of the target polynucleotide as a template for the sequencing polymerization reactions.

Especially in situations where a sequence is generally known, the entirety of a long DNA target strand can be sequenced using this primer walking approach. One application of such a procedure would be the identification of mutations or alternate alleles.

As schematically illustrated in FIG. 8, a plurality of different probe/primers can be respectively placed in different reaction chambers corresponding to parallel gel channels, and the same target DNA sequence can be sequenced from different positions of that target DNA sequence. This allows a long target DNA to be completely sequenced in parallel lanes.

Once the sequencing reactions are completed, the family of strands in each well must be separated according to size so that the nucleotide sequence can be determined. The strands must first be freed from the solid support. Two protocols are suggested: first, simply thermally or chemically melting the newly synthesized strand from the linker oligonucleotide, as in FIG. 5(b), or secondly by chemically, photochemically or enzymatically cleaving a site built into the linker or the probe/primer, as in the method of FIG. 6.

Separation is achieved by applying a voltage to propel the nucleotide strand into the gel. A normal value for separation electrophoresis is about 200 v/cm with a working range of 50 to 1500 v/cm. Current, voltage or power can be controlled in the electrophoretic separation of the present invention. The short length will require only a small voltage compared to the approximately 2000 volts or more used in conventional sequencing gel electrophoresis. The microarchitecture and resultant small cross section allows the use of low current and low power supplies. Prototypical experiments using 200 to 300 v/cm result in a current of 10 to 50 μa per lane.

Alternatively, the small cross section of the separating lanes allows more efficient cooling which permits faster separations at higher current densities.

One advantage to the planar microchip of the present invention is that with laser induced fluorescence the point of detection can be placed anywhere along the parallel channels 16 and 18. Detection of the separated bands and determination of the sequence can be accomplished by any means known in the art.

The preferred embodiment uses a scanning laser to excite fluorophores attached to the terminal nucleotides of each strand. Plural laser sources having plural excitation wavelengths may be used.

Alternatively a color wheel interposed between the microchip and a photomultiplier tube (PMT) may be used to filter fluorescent emissions. A charge coupled device camera (CCD) could also be used. When using a PMT lanes and bands within lanes can be identified by time tagging, a) the laser as it scans and/or b) the color wheel as it spins. The CCD itself provides positional information.

While advantageous embodiments have been chosen to illustrate the invention, it will be understood by those skilled in the art that various changes and modifications can be made therein without departing from the scope of the invention as defined in the appended claims.

What is claimed is:

1. An apparatus for performing DNA sequencing, comprising:
   a) a body comprising a substrate and a cover plate bonded thereto wherein said coverplate is transparent;
   b) a channel pattern formed within said body and including at least one gel channel having a first and second longitudinal ends and being at least partially filled with gel;
   c) a reaction chamber in communication with said gel and having attached thereto photocleavable linkers wherein said photocleavable linkers have bound thereto oligonucleotide probes/primers;
   d) means for communicating a solution containing at least one target DNA to said reaction chamber for hybridization with said DNA synthesis primers; and
   e) means for establishing an electric field between said first and second longitudinal ends of said at least one gel channel, of sufficient strength to impart electrophoretic separation of chain-terminated strands of DNA through said gel.

2. The apparatus of claim 1, wherein said body comprises either silicon, glass, quartz, plastic, or ceramics.

3. The apparatus according to claim 2, wherein the substrate is made of optically transparent material.

4. The apparatus according to claim 1, wherein said channel pattern includes a plurality of gel channels, and said communicating means comprises at least one manifold connecting channel interconnecting said plurality of gel channels at one common end.

5. The apparatus according to claim 1, wherein said means for establishing an electric field comprises first and second electrodes disposed respectively at said first and second opposite ends of said at least one gel channel, and a d.c. power source coupled to said first and second electrodes.

6. The apparatus according to claim 1 wherein said cover plate has access ports for the introduction of substances into said reaction chamber.

7. A method of making a nucleic acid sedquencing microchip apparatus comprising the steps of:
   a) forming a channel pattern in a planar surface of a substrate, said channel pattern including at least one gel channel;
   b) fixedly attaching a cover plate on said planar surface of said substrate;
   c) partially filling said at least one gel channel with a gel, and thereby forming a reaction chamber in the unfilled portion wherein said reaction chamber has attached thereto photocleavable linkers wherein said photocleavable linkers have bound thereto oligonucleotide probes/primers; and
   d) placing first and second electrodes respectively at opposite ends of said at least one gel channel.

8. The method according to claim 7, wherein said step of partially filling said at least one gel channel includes filling said at least one gel channel with an acrylamide buffer solution, covering said reaction chamber portion of said gel channel with a photo-blocker, photopolymerizing said acrylamide solution within said parallel channels with a light source, whereby acrylamide in said reaction chamber is not polymerized, and then flushing out the remaining acrylamide.

9. The method according to claim 8, wherein said filling step includes electro-osmotically pumping said acrylamide buffer solution into said at least one gel channel.

10. The method according to claim 7, wherein said step of forming a channel pattern includes etching the channel pattern into, said planar surface of said substrate using photolithographic techniques.

11. The method according to claim 7, wherein said step of forming a channel pattern includes micro-machining said channel pattern.

12. The method according to claim 7, wherein said step of forming a channel pattern includes forming a plurality of parallel gel channels, and forming at least one manifold connecting channel that interconnects said plurality of parallel gel channels.

13. An apparatus for simultaneously sequencing a plurality of polynucleic acids comprising:
   a) a solid support substrate;
   b) a plurality of sequencing channels, each said channel having a reaction well and a separating zone;
   c) means for delivering substances to each said reaction well;
   d) means for specifically selecting and binding a predetermined target sequence within said reaction well of each said channel;
   e) means for individually controlling sequencing reactions in each said reaction well;
   f) photocleavable linkers bound to said reaction wells and wherein said photocleavable linkers have bound thereto oligonucleotide probes/primers;
   g) means for applying an electrophoretic voltage across separating zone;
   h) means for monitoring said electrophoretic separation to determine a sequence of a polynucleic acid from the target sequence in each said reaction well; and
   i) a transparent cover plate fixedly attached to said substrate.

14. The apparatus according to claim 13, wherein said solid support substrate is a glass microchip.

15. The apparatus according to claim 13, wherein said plurality of sequencing channels are formed by etching.

16. The apparatus of according to claim 13, wherein said means for delivering substances to each of said reaction wells comprises at least one manifold connecting channel that intersects each of said reaction wells.

17. The apparatus according to claim 16, wherein said means for delivering substances to each said reaction well further comprises an additional manifold connecting channel that intersects each of said reaction wells and being disposed between said reaction well and said separation zone.

18. The apparatus according to claim 16, wherein said means for delivering substances to each said reaction well further comprises electro-osmotic means for pumping reaction compounds through said manifold connecting channel to said reaction well of each said sequencing channel.

19. The apparatus according to claim 13, wherein said means for specifically selecting and binding a predetermined target sequence within said reaction well of each said sequencing channel comprises a linker compound covalently bonded to a primer compound wherein said primer compound is capable of priming a synthetic reaction.

20. The apparatus according to claim 13, wherein said means for specifically selecting and binding a predetermined target sequence within said reaction well of each said sequencing channel comprises a probe/primer compound complementarily hydrogen bonded to a linker compound.

21. The apparatus according to claim 13, wherein said means for applying electrophoretic voltage comprises first and second electrodes disposed at opposite ends of said plurality of sequencing channels.

22. The apparatus according to claim 13, wherein said plurality of sequencing channels number between 50 and 10,000.

23. The apparatus according to claim 13, wherein each sequencing channel is between 10 and 100 μm in width.

24. The apparatus according to claim 13, wherein said means for monitoring said electrophoretic separation comprises plural fluorescent labels, each of said fluorescent labels indicating one nucleotide base, where said nucleotide base is an element of the sequence of the polynucleic acid of said reaction well.

25. The apparatus according to claim 13 wherein said cover plate has access ports for the introduction of substances into said reaction wells.

* * * * *